(12) United States Patent
Savage

(10) Patent No.: US 12,030,912 B2
(45) Date of Patent: *Jul. 9, 2024

(54) CATIONIC STEROIDAL ANTIMICROBIAL COMPOUNDS WITH URETHANE LINKAGES

(71) Applicant: Paul B. Savage, Mapleton, UT (US)

(72) Inventor: Paul B. Savage, Mapleton, UT (US)

(73) Assignee: Brigham Young University, Provo, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/318,206

(22) Filed: May 12, 2021

(65) Prior Publication Data

US 2021/0355155 A1 Nov. 18, 2021

Related U.S. Application Data

(60) Provisional application No. 63/025,255, filed on May 15, 2020.

(51) Int. Cl.
*C07J 9/00* (2006.01)
*A61P 31/04* (2006.01)

(52) U.S. Cl.
CPC .............. *C07J 9/005* (2013.01); *A61P 31/04* (2018.01)

(58) Field of Classification Search
CPC .................................................. C07J 41/0061
See application file for complete search history.

(56) References Cited

U.S. PATENT DOCUMENTS

| | | | |
|---|---|---|---|
| 2007/0191322 A1 | 8/2007 | Savage et al. | |
| 2018/0169114 A1 | 6/2018 | Genberg et al. | |
| 2020/0368253 A1* | 11/2020 | Savage | A61Q 7/00 |

FOREIGN PATENT DOCUMENTS

| | | | |
|---|---|---|---|
| WO | WO-2009005258 A2 * | 1/2009 | ........ A61K 47/48107 |
| WO | 2019/173642 A1 | 9/2019 | |

OTHER PUBLICATIONS

Sokolova et al. (Russian Journal of Bioorganic Chemistry, 2004, 30(5), pp. 477-481).*
Bandyopadhyay et al. (J. Am. Chem. Soc., 2001, 123, pp. 7691-7696).*

(Continued)

*Primary Examiner* — Susanna Moore
(74) *Attorney, Agent, or Firm* — Workman Nydegger

(57) ABSTRACT

Cationic steroidal antimicrobial (CSA) compounds having a structure of Formula I, II or III, or salt thereof, wherein at least one of at least one of $R_1$-$R_{18}$, (e.g., $R_3$, $R_7$ and $R_{12}$) is linked to the steroidal backbone by a urethane group:

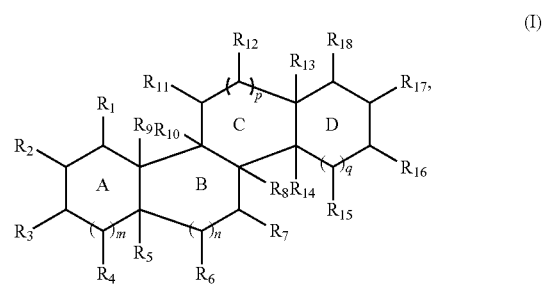

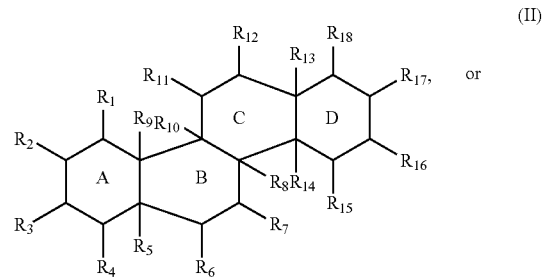

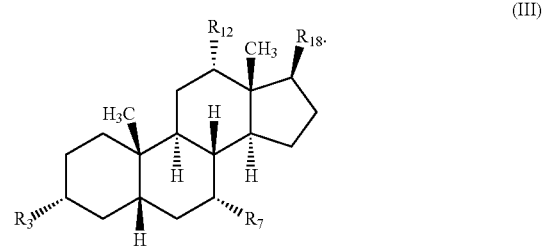

At least one of $R_1$-$R_{18}$, (e.g., $R_3$, $R_7$ and $R_{12}$) has the following urethanyl structure:

—O—(C=O)—$NR_{19}R_{20}$ where $R_{19}$ and $R_{20}$ are independently hydrogen, alkyl, alkenyl, alkynyl, aryl, aminoalkyl, aminoalkenyl, aminoalkynyl, or aminoaryl, provided that at least one of $R_{19}$ or $R_{20}$ includes an amino group (e.g., $R_{19}$ is hydrogen and $R_{20}$ is ($C_2$-$C_6$)aminoalkyl).
$R_{18}$ can have the following structure:

—$R_{21}$—(C=O)—$NR_{22}R_{23}$ where $R_{21}$ is omitted or alkyl, alkenyl, alkynyl, or aryl, and $R_{22}$ and $R_{23}$ are hydrogen, alkyl, alkenyl, alkynyl, or aryl, provided that at least one of $R_{22}$ or $R_{23}$ is not hydrogen.

17 Claims, No Drawings

(56) References Cited

OTHER PUBLICATIONS

International Search Report and Written Opinion received for PCT Patent Application No. PCT/US21/32208, dated Sep. 28, 2021, 10 pages.
Invitation to Pay Additional Fees received for PCT Patent Application No. PCT/US21/032208, dated Jul. 6, 2021. 2 pages.
Pubchem, SID 275181444, Modify Date: Nov. 21, 2016 [retrieved on Aug. 19, 2021). Retrieved from the Internet: <URL: https://pubchem.ncbi.nlm.nih.gov/substance/275181444> entire document.
Pubchem, SID 389021670, Available Date: Dec. 6, 2019 [retrieved on Jun. 14, 2021). Retrieved from the Internet: <URL: https://pubchem.ncbi.nlm.nih.gov/substance/389021670> entire document.
European Search Report received for EP Patent Application No. 21804364.4, mailed on May 16, 2024, 07 pages.

\* cited by examiner

CATIONIC STEROIDAL ANTIMICROBIAL COMPOUNDS WITH URETHANE LINKAGES

CROSS-REFERENCE TO RELATED APPLICATIONS

This Application claims the benefit of U.S. Provisional Application No. 63/025,255, filed May 15, 2020, which is incorporated by reference in its entirety.

BACKGROUND OF THE INVENTION

1. Field

The invention relates to cationic steroidal antimicrobial (CSA) compounds, including CSA compounds having urethane linkages, and methods of manufacturing CSA compounds having urethane linkages.

2. Related Technology

Antimicrobial peptides are found in organisms ranging from mammals to amphibians to insects to plants. The ubiquity of antimicrobial peptides has been used as evidence that these compounds do not readily engender bacterial resistance. In addition, considering the varied sequences of antimicrobial peptides among diverse organisms, it is apparent that they have evolved independently multiple times. Thus, antimicrobial peptides appear to be one of "Nature's" primary means of controlling bacterial growth. For example, endogenous antimicrobial peptides, such as the human cathelicidin LL-37, play key roles in innate immunity. LL-37 is found in airway mucus and is believed to be important in controlling bacterial growth in the lung. However, clinical use of antimicrobial peptides presents significant issues including the relatively high cost of producing peptide-based therapeutics, the susceptibility of peptides to proteases generated by the host and by bacterial pathogens, and deactivation of antimicrobial peptides by proteins and DNA in lung mucosa.

An attractive means of harnessing the antibacterial activities of antimicrobial peptides without the issues delineated above is to develop non-peptide mimics of antimicrobial peptides that display similar broad-spectrum antibacterial activity utilizing the same or similar mechanism of action. Non-peptide mimics would offer lower-cost synthesis and potentially increased stability to proteolytic degradation. In addition, control of water solubility and charge density may be used to control association with proteins and DNA in lung mucosa.

With over 1,600 examples of known antimicrobial peptides, it is possible to categorize the structural features common to them. While the primary sequences of these peptides vary substantially, morphologies adopted by a vast majority are similar. Those that adopt alpha helix conformations juxtapose hydrophobic side chains on one face of the helix with cationic (positively charged) side chains on the opposite side. Similar morphology is found in antimicrobial peptides that form beta sheet structures: hydrophobic side chains on one face of the sheet and cationic side chains on the other.

Examples of small molecule, non-peptide mimics of antimicrobial peptides, include steroidal compounds known as "ceragenins," an example of which is "CSA-13," which can reproduce the amphiphilic morphology in antimicrobial peptides. A problem that remains is that CSA compounds often require complex, multi-step reaction sequences for their manufacture. Every additional step in the manufacture of CSA compounds increases cost and reduces overall product yield. Accordingly, there remains a need to identify CSA compounds that are easier and less expensive to manufacture while possessing desired antimicrobial, anti-inflammatory, and other desirable properties and effects.

SUMMARY

Disclosed herein is a new class of cationic steroidal antimicrobial (CSA) compounds with urethane groups that link one or more side group to the sterol backbone. The urethane-linked CSA compounds are easier and less expensive to manufacture and yet possess desired antimicrobial, anti-inflammatory, and other desirable properties.

The CSA compounds, including salts thereof, disclosed herein can have a structure of Formula I, II or III, which has a fused ring steroidal backbone and wherein at least one of at least one of $R_1$-$R_{18}$, preferably at least one of $R_3$, $R_7$ and $R_{12}$, is linked to the steroidal backbone by a urethane group:

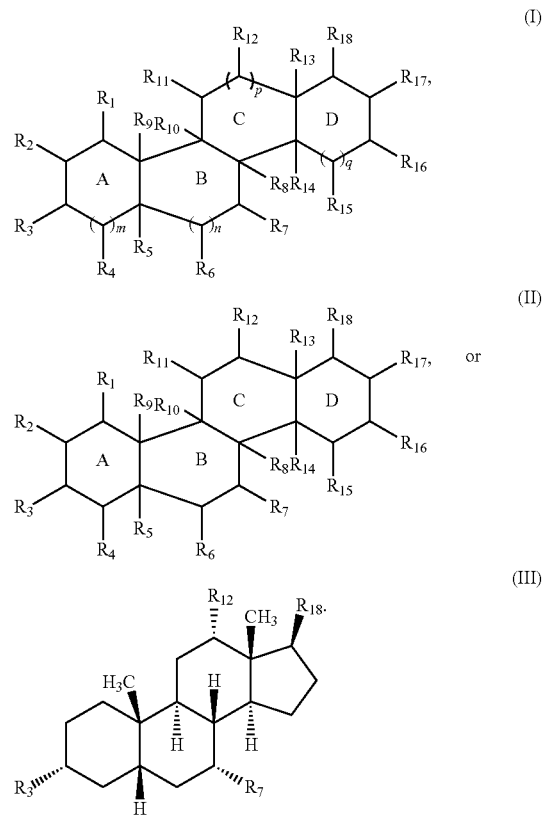

In embodiments, at least one of at least one of $R_1$-$R_{18}$, preferably at least one of $R_3$, $R_7$ and $R_{12}$, can have the following urethanyl structure:

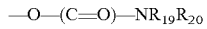

where $R_{19}$ and $R_{20}$ are independently selected from hydrogen, alkyl, alkenyl, alkynyl, aryl, aminoalkyl, aminoalkenyl, aminoalkynyl, and aminoaryl, provided that at least one of $R_{19}$ or $R_{20}$ includes an amino group, preferably where $R_{19}$ is hydrogen and $R_{20}$ is $(C_2$-$C_6)$aminoalkyl.

In embodiments, $R_{18}$ can have the following structure:

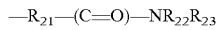

where $R_{21}$ is omitted or is selected from alkyl, alkenyl, alkynyl, or aryl, and $R_{22}$ and $R_{23}$ are independently selected from hydrogen, alkyl, alkenyl, alkynyl, and aryl, provided that at least one of $R_{22}$ or $R_{23}$ is not hydrogen.

Non-limiting examples of CSA compounds in which at least one of $R_3$, $R_7$ and $R_{12}$ is attached to the steroidal backbone by a urethane linkage are CSA-255, CSA-256, CSA-257, CSA-258, and salts thereof:

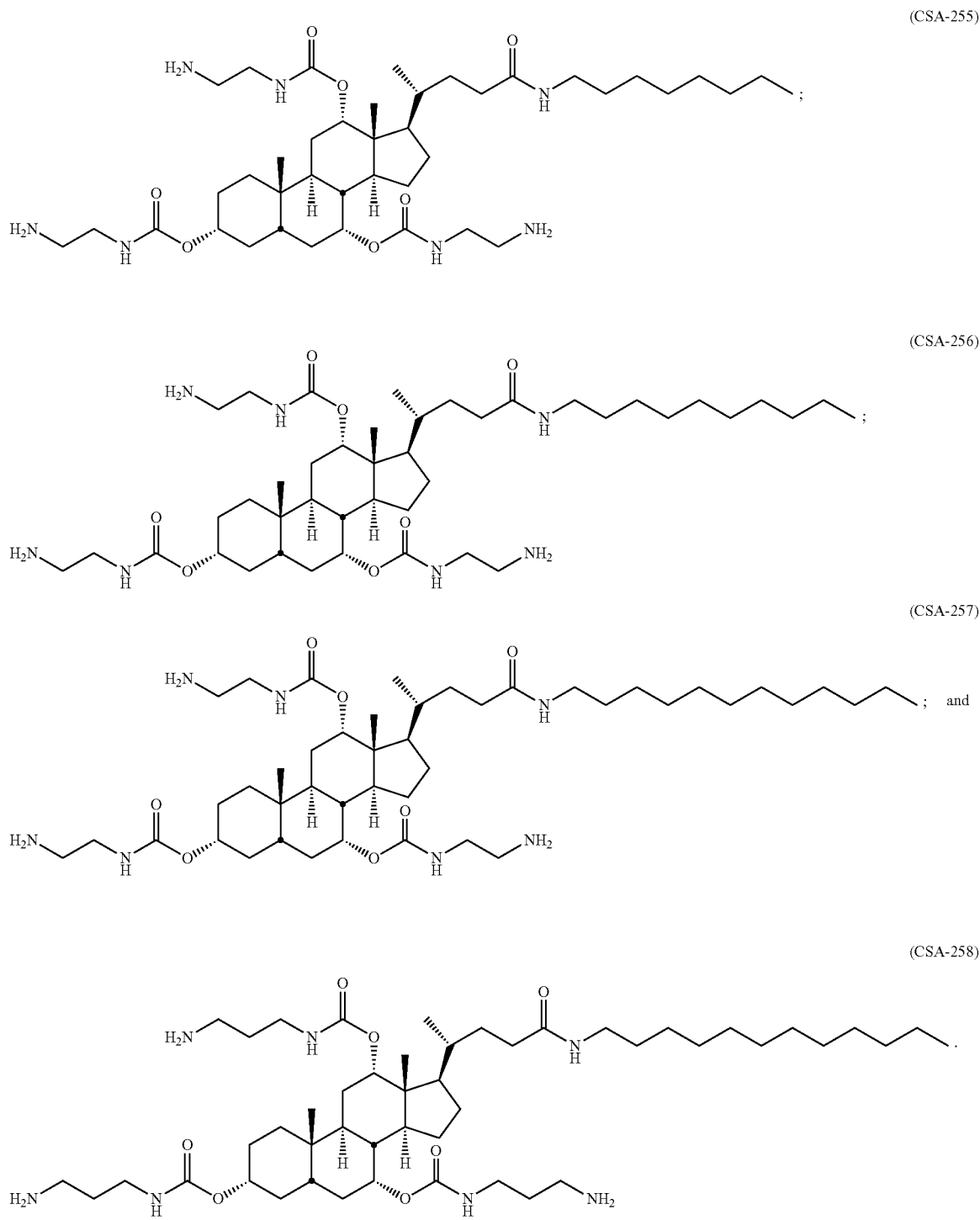

In embodiments, a method of manufacturing a CSA compound having urethane linkages as disclosed herein includes: (1) optionally reacting or protecting the acidic group of cholic acid in one or more steps to form $R_{18}$, such as by forming an amide at the C24 position, and (2) reacting at least one of the hydroxyl groups at the C3, C7 and C12 positions of cholic acid in one or more steps to form a urethane linkage, which links at least one of $R_3$, $R_7$ and $R_{12}$ to the sterol backbone to yield a desired CSA compound.

Advantages of the CSA compounds disclosed herein include, but are not limited to, comparable and/or improved antimicrobial activity, anti-inflammatory activity, and other desired properties compared to existing CSA compounds and/or simplified synthetis of CSA compounds and/or intermediate CSA compounds compared to existing synthetic routes.

Additional features and advantages will be set forth in part in the description that follows, and in part will be obvious from the description, or may be learned by practice of the embodiments disclosed herein. It is to be understood that both the foregoing brief summary and the following detailed description are exemplary and not restrictive of the embodiments disclosed herein or as claimed.

DETAILED DESCRIPTION

Disclosed herein is a new class of cationic steroidal antimicrobial (CSA) compounds with urethane functional groups that link one or more side group to the sterol backbone. The urethane-linked CSA compounds are easier and less expensive to manufacture and yet possess desired antimicrobial, anti-inflammatory, and other desirable properties.

Definitions

Any "R" groups such as, without limitation, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$, represent substituents that can be attached to the sterol backbone. Unless otherwise specified, an R group may be substituted or unsubstituted.

A "ring" as used herein can be heterocyclic or carbocyclic. "Saturated" refers to a ring in which each atom is either hydrogenated or substituted such that the valency of each atom is filled. "Unsaturated" refers to a ring where the valency of each atom of the ring may not be filled with hydrogen or other substituents. For example, adjacent carbon atoms in a fused ring can be double bound to each other. Unsaturation can also include deleting at least one of the following pairs and completing the valency of the ring carbon atoms at these deleted positions with a double bond, such as $R_5$ and $R_9$; $R_8$ and $R_{10}$; and $R_{13}$ and $R_{14}$.

Where a group is "substituted" it may be substituted with one, two, three or more of the indicated substituents, which may be the same or different, each replacing a hydrogen atom. If no substituents are indicated, the indicated "substituted" group may be substituted with one or more groups individually and independently selected from alkyl, alkenyl, alkynyl, cycloalkyl, cycloalkenyl, cycloalkynyl, acylalkyl, alkoxyalkyl, aminoalkyl, amino acid, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen (e.g., F, Cl, Br, and I), thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, oxo, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, $R_aO(CH_2)_mO$—, $R_b(CH_2)_nO$—, $R_cC(O)O(CH_2)_pO$—, and protected derivatives thereof. The substituent may be attached to the group at more than one attachment point. For example, an aryl group may be substituted with a heteroaryl group at two attachment points to form a fused multicyclic aromatic ring system. Biphenyl and naphthalene are two examples of an aryl group that is substituted with a second aryl group. A group that is not specifically labeled as substituted or unsubstituted may be considered to be either substituted or unsubstituted.

The terms "$C_a$" or "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

"Urethanyl" refers to "—O—(C═O)—$NR_{19}R_{20}$" as defined more fully herein.

"Alkyl" refers to a straight or branched hydrocarbon chain that comprises a fully saturated (no double or triple bonds) hydrocarbon group. The alkyl group may have 1 to 25 carbon atoms (whenever it appears herein, a numerical range such as "1 to 25" refers to each integer in the given range; e.g., "1 to 25 carbon atoms" means that the alkyl group may consist of 1 carbon atom, 2 carbon atoms, 3 carbon atoms, etc., up to and including 25 carbon atoms, although the present definition also covers the occurrence of the term "alkyl" where no numerical range is designated). The alkyl group may also be a medium size alkyl having 1 to 15 carbon atoms. The alkyl group could also be a lower alkyl having 1 to 6 carbon atoms. The alkyl group of the compounds may be designated as "$C_4$" or "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, isopropyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

"Alkenyl" refers to an alkyl group that contains in the straight or branched hydrocarbon chain one or more double bonds. The alkenyl group may have 2 to 25 carbon atoms (whenever it appears herein, a numerical range such as "2 to 25" refers to each integer in the given range; e.g., "2 to 25 carbon atoms" means that the alkenyl group may consist of 2, 3, or 4 carbon atoms, etc., up to and including 25 carbon atoms, although the present definition also covers the occurrence of the term "alkenyl" where no numerical range is designated). The alkenyl group may also be a medium size alkenyl having 2 to 15 carbon atoms. The alkenyl group could also be a lower alkenyl having 1 to 6 carbon atoms. The alkenyl group of the compounds may be designated as "$C_4$" or "$C_2$-$C_4$ alkenyl" or similar designations. An alkenyl group may be unsubstituted or substituted.

"Alkynyl" refers to an alkyl group that contains in the straight or branched hydrocarbon chain one or more triple bonds. The alkynyl group may have 2 to 25 carbon atoms (whenever it appears herein, a numerical range such as "2 to 25" refers to each integer in the given range; e.g., "2 to 25 carbon atoms" means that the alkynyl group may consist of 2, 3, or 4 carbon atoms, etc., up to and including 25 carbon atoms, although the present definition also covers the occurrence of the term "alkynyl" w.53here no numerical range is designated). The alkynyl group may also be a medium size alkynyl having 2 to 15 carbon atoms. The alkynyl group could also be a lower alkynyl having 2 to 6 carbon atoms. The alkynyl group of the compounds may be designated as "$C_4$" or "$C_2$-$C_4$ alkynyl" or similar designations. An alkynyl group may be unsubstituted or substituted.

"Aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group (although the definition of $C_6$-$C_{10}$ aryl covers the occurrence of "aryl" when no numerical range is designated). Examples of aryl groups include, but are not limited to, benzene, naphthalene and azulene. An aryl group may be substituted or unsubstituted.

"Aralkyl" and "aryl(alkyl)" refer to an aryl group connected, as a substituent, via a lower alkylene group. The aralkyl group may have 6 to 20 carbon atoms (whenever it appears herein, a numerical range such as "6 to 20" refers to each integer in the given range; e.g., "6 to 20 carbon atoms" means that the aralkyl group may consist of 6 carbon atom, 7 carbon atoms, 8 carbon atoms, etc., up to and including 20 carbon atoms, although the present definition also covers the occurrence of the term "aralkyl" where no numerical range is designated). The lower alkylene and aryl group of an aralkyl may be substituted or unsubstituted. Examples include but are not limited to benzyl, 2-phenylalkyl, 3-phenylalkyl, and naphthylalkyl.

"Lower alkylene groups" refers to a $C_1$-$C_{25}$ straight-chained alkyl tethering groups, such as —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

"Cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

"Cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

"Cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

"Alkoxy" or "alkyloxy" refer to the formula —OR wherein R is an alkyl, an alkenyl, an alkynyl, a cycloalkyl, a cycloalkenyl or a cycloalkynyl as defined above. A non-limiting list of alkoxys are methoxy, ethoxy, n-propoxy, 1-methylethoxy (isopropoxy), n-butoxy, iso-butoxy, sec-butoxy and tert-butoxy. An alkoxy may be substituted or unsubstituted.

"Acyl" refers to a hydrogen, alkyl, alkenyl, alkynyl, aryl, or heteroaryl connected, as substituents, via a carbonyl group, such as —(C=O)—R. Examples include formyl, acetyl, propanoyl, benzoyl, and acryl. An acyl may be substituted or unsubstituted.

"Alkoxyalkyl" or "alkyloxyalkyl" refer to an alkoxy group connected, as a substituent, via a lower alkylene group. Examples include alkyl-O-alkyl- and alkoxy-alkyl- with the terms alkyl and alkoxy defined herein.

"Hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

"Haloalkyl" refers to an alkyl group in which one or more of the hydrogen atoms are replaced by a halogen (e.g., mono-haloalkyl, di-haloalkyl and tri-haloalkyl). Examples include chloromethyl, fluoromethyl, difluoromethyl, trifluoromethyl and 1-chloro-2-fluoromethyl, 2-fluoroisobutyl. A haloalkyl may be substituted or unsubstituted.

"Amino" refers to "—$NH_2$".

"Hydroxy" refers to "—OH".

"Cyano" refers to "—CN".

"Carbonyl" or "oxo" refer to "—C=O".

"Azido" refers to "—$N_3$".

"Aminoalkyl" refers to an amino group connected, as a substituent, via a lower alkylene group. Examples include $H_2$N-alkyl- with the term alkyl defined herein.

"Alkylcarboxyalkyl" refers to an alkyl group connected, as a substituent, to a carboxy group that is connected, as a substituent, to an alkyl group. Examples include alkyl-(C=O)—O-alkyl- and alkyl-O—(C=O)-alkyl- with the term alkyl as defined herein.

"Alkylaminoalkyl" refers to an alkyl group connected, as a substituent, to an amino group that is connected, as a substituent, to an alkyl group. Examples include alkyl-NH-alkyl- with the term alkyl as defined herein.

"Dialkylaminoalkyl" and "di(alkyl)aminoalkyl" refer to two alkyl groups connected, each as a substituent, to an amino group that is connected, as a substituent, to an alkyl group. Examples include

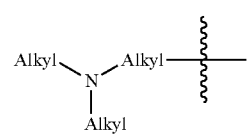

with the term alkyl as defined herein.

"Alkylaminoalkylamino" refers to an alkyl group connected, as a substituent, to an amino group that is connected, as a substituent, to an alkyl group that is connected, as a substituent, to an amino group. Examples include alkyl-NH-alkyl-NH— with the term alkyl as defined herein.

"Alkylaminoalkylaminoalkylamino" refers to an alkyl group connected, as a substituent, to an amino group that is connected, as a substituent, to an alkyl group that is connected, as a substituent, to an amino group that is connected, as a substituent, to an alkyl group. Examples include alkyl-NH-alkyl-NH-alkyl- with the term alkyl as defined herein.

"Arylaminoalkyl" refers to an aryl group connected, as a substituent, to an amino group that is connected, as a substituent, to an alkyl group. Examples include aryl-NH-alkyl- with the terms aryl and alkyl as defined herein.

"Aminoalkyloxy" refers to an amino group connected, as a substituent, to an alkyloxy group. Examples include $H_2N$-alkyl-O— and $H_2N$-alkoxy- with the terms alkyl and alkoxy as defined herein.

"Aminoalkyloxyalkyl" refers to an amino group connected, as a substituent, to an alkyloxy group connected, as a substituent, to an alkyl group. Examples include $H_2N$-alkyl-O-alkyl- and $H_2N$-alkoxy-alkyl- with the terms alkyl and alkoxy as defined herein.

"Aminoalkylcarboxy" refers to an amino group connected, as a substituent, to an alkyl group connected, as a substituent, to a carboxy group. Examples include $H_2N$-alkyl-(C=)—O— and $H_2N$-alkyl-O—(C=O)— with the term alkyl as defined herein.

"Aminoalkylaminocarbonyl" refers to an amino group connected, as a substituent, to an alkyl group connected, as a substituent, to an amino group connected, as a substituent, to a carbonyl group. Examples include $H_2N$-alkyl-NH—(C=O)— with the term alkyl as defined herein.

"Aminoalkylcarboxamido" refers to an amino group connected, as a substituent, to an alkyl group connected, as a substituent, to a carbonyl group connected, as a substituent to an amino group. Examples include $H_2N$-alkyl-(C=O)—NH— and $H_2N$-alkyl-NH—(C=O)— with the term alkyl as defined herein.

"Azidoalkyloxy" refers to an azido group connected as a substituent, to an alkyloxy group. Examples include $N_3$-alkyl-O— and $N_3$-alkoxy- with the terms alkyl and alkoxy as defined herein.

"Cyanoalkyloxy" refers to a cyano group connected as a substituent, to an alkyloxy group. Examples include NC-alkyl-O— and NC-alkoxy- with the terms alkyl and alkoxy as defined herein.

"Sulfenyl" refers to "—SR" in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. A sulfenyl may be substituted or unsubstituted.

"Sulfinyl" refers to "—(S=O)—R" in which R can be the same as defined with respect to sulfenyl. A sulfinyl may be substituted or unsubstituted.

"Sulfonyl" refers to "—(S=O)—OR" in which R can be the same as defined with respect to sulfenyl. A sulfonyl may be substituted or unsubstituted.

"O-carboxy" refers to "R—(C=O)—O—" in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined herein. An O-carboxy may be substituted or unsubstituted.

"Ester" and "C-carboxy" refer to "—(C=O)—OR" in which R can be the same as defined with respect to O-carboxy. An ester and C-carboxy may be substituted or unsubstituted.

"Thiocarbonyl" refers to "—(C=S)—R" in which R can be the same as defined with respect to O-carboxy. A thiocarbonyl may be substituted or unsubstituted.

"Trihalomethanesulfonyl" refers to "$X_3CSO_2$—" wherein X is a halogen.

"S-sulfonamido" refers to "—$SO_2$N(RARB)" in which RA and RB can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An S-sulfonamido may be substituted or unsubstituted.

"N-sulfonamide" refers to "$RSO_2$N(RA)-" in which R and RA can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-sulfonamido may be substituted or unsubstituted.

"O-carbamyl" refers to "—O—(C=O)—N(RARB)" in which RA and RB can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An O-carbamyl may be substituted or unsubstituted.

"N-carbamyl" refers to "RO—(C=O)—N(RA)-" in which R and RA can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-carbamyl may be substituted or unsubstituted.

"O-thiocarbamyl" refers to "—O—(C=S)—N(RARB)" in which RA and RB can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An O-thiocarbamyl may be substituted or unsubstituted.

"N-thiocarbamyl" refers to "RO—(C=S)—N(RA)-" in which R and RA can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-thiocarbamyl may be substituted or unsubstituted.

C-amido" refers to "—(C=O)—N(RARB)" in which RA and RB can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. A C-amido may be substituted or unsubstituted.

"N-amido" refers to "R—(C=O)—N(RA)-" in which R and RA can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-amido may be substituted or unsubstituted.

"Guanidinoalkyloxy" refers to a guanidinyl group connected, as a substituent, to an alkyloxy group. Examples include

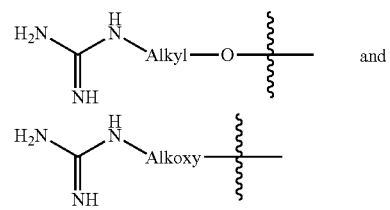

with the terms alkyl and alkoxy as defined herein.

"Guanidinoalkylcarboxy" refers to a guanidinyl group connected, as a substituent, to an alkyl group connected, as a substituent, to a carboxy group. Examples include

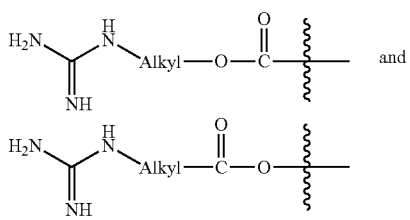

with the term alkyl as defined herein.

"Quaternary ammonium alkylcarboxy" refers to a quaternized amino group connected, as a substituent, to an alkyl group connected, as a substituent, to a carboxy group. Examples include

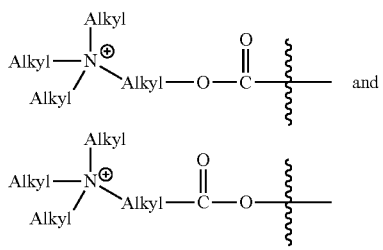

with the term alkyl as defined herein.

"Halogen atom" and "halogen" mean any one of the radio-stable atoms of column 7 of the Periodic Table of the Elements, such as, fluorine, chlorine, bromine and iodine.

Where the number of substituents is not specified (e.g. haloalkyl), there may be one or more substituents present. For example, "haloalkyl" may include one or more of the same or different halogens.

"Amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, γ-aminobutyric acid, citrulline, β-alanine, α-ethylglycine, α-propyl-glycine and norleucine.

A linking group is a divalent moiety used to link one steroid to another steroid. In embodiments, the linking group is used to link a first CSA with a second CSA (which may be the same or different). An example of a linking group is $(C_1-C_{10})$ alkyloxy-$(C_1-C_{10})$ alkyl.

"P.G." or "protecting group" or "protecting groups" refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4"-trimethoxytrityl (TMTr); and those described herein). Amino-protecting groups are known to those skilled in the art. In general, the species of protecting group is not critical, provided that it is stable to the conditions of any subsequent reaction(s) on other positions of the compound and can be removed at the appropriate point without adversely affecting the remainder of the molecule. In addition, a protecting group may be substituted for another after substantive synthetic transformations are complete. Clearly, where a compound differs from a compound disclosed herein only in that one or more protecting groups of the disclosed compound has been substituted with a different protecting group, that compound is within the disclosure.

CSA Compounds:

Cationic steroidal anti-microbial (CSA) compounds, also referred to as "CSA compounds", "CSAs", CSA molecules or "ceragenin" compounds, are synthetically produced, small molecule chemical compounds that include a sterol backbone having various charged groups (e.g., amine and cationic groups) attached to the backbone. The sterol backbone can be used to orient amine or guanidine groups on a face or plane of the sterol backbone. CSAs are cationic and amphiphilic, based upon the functional groups attached to the backbone. They are facially amphiphilic with a hydrophobic face and a polycationic face.

Without wishing to be bound to theory, CSA molecules described herein act as anti-microbial agents (e.g., anti-bacterial, anti-fungal, and anti-viral). It is believed, for example, that anti-microbial CSA molecules may act as an anti-microbial by binding to the cellular membrane of bacteria and other microbes and modifying the cell membrane, e.g., such as by forming a pore that allows the leakage of ions and cytoplasmic materials critical to the microbe's survival, and leading to the death of the affected microbe. In addition, anti-microbial CSA molecules may also act to sensitize bacteria to other antibiotics. For example, at concentrations of anti-microbial CSA molecules below the corresponding minimum bacteriostatic concentration (MIC), the CSA compound may cause bacteria to become more susceptible to other antibiotics by disrupting the cell membrane, such as by increasing membrane permeability. It is postulated that charged cationic groups may be responsible for disrupting the bacterial cellular membrane and imparting anti-microbial properties. CSA molecules may have similar membrane- or outer coating-disrupting effects on fungi and viruses.

By way of background, exemplary CSA compounds and methods for their manufacture are described in U.S. Pat. Nos. 6,350,738, 6,486,148, 6,767,904, 7,598,234, 7,754,705, 8,691,252, 8,975,310, 9,434,759, 9,527,883, 9,943,614, 10,155,788, 10,227,376, 10,370,403, and 10,626,139, and U.S. Pat. Pub. Nos. 2016/0311850 and 2017/0210776, which are incorporated herein by reference. The skilled artisan will recognize the compounds within the generic formulae set forth herein and understand their preparation in view of the references cited herein and the Examples.

The compounds and compositions disclosed herein are optionally prepared as salts, which advantageously makes them cationic when one or more amine groups is/are protonated. The term "salt" as used herein is a broad term and is to be given its ordinary and customary meaning to a skilled artisan (and is not to be limited to a special or customized meaning), and refers without limitation to a salt of a compound. In embodiments, the salt is an acid addition salt of the compound. Salts can be obtained by reacting a compound with inorganic acids such as hydrohalic acid (e.g., hydrochloric acid or hydrobromic acid), sulfuric acid, nitric acid, phosphoric acid, and phosphonic acid. Salts can also be obtained by reacting a compound with an organic acid such as aliphatic or aromatic carboxylic or sulfonic acids, sulfinic acids, for example formic acid, acetic acid, propionic acid, glycolic acid, pyruvic acid, malonic acid, maleic acid, fumaric acid, trifluoroacetic acid, benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or 1,5-naphthalenedisulfonic acid. Salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, $C_1$-$C_7$ alkylamine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like.

In embodiments, the salt is a hydrochloride salt. In embodiments, the salt is a mono-hydrochloride salt, a di-hydrochloride salt, a tri-hydrochloride salt, or a tetra-hydrochloride salt. Additional examples of salts include sulfuric acid addition salts, sulfonic acid addition salts, disulfonic acid addition salts, 1,5-naphthalenedisulfonic acid addition salts, sulfate salts, and bisulfate salts.

The CSA compounds disclosed herein can have a structure of Formula I, II or III, or a salt thereof, having a steroidal backbone, and wherein at least one of at least one of $R_1$-$R_{18}$, preferably at least one of $R_3$, $R_7$ and $R_{12}$, is linked to the steroidal backbone by a urethane group:

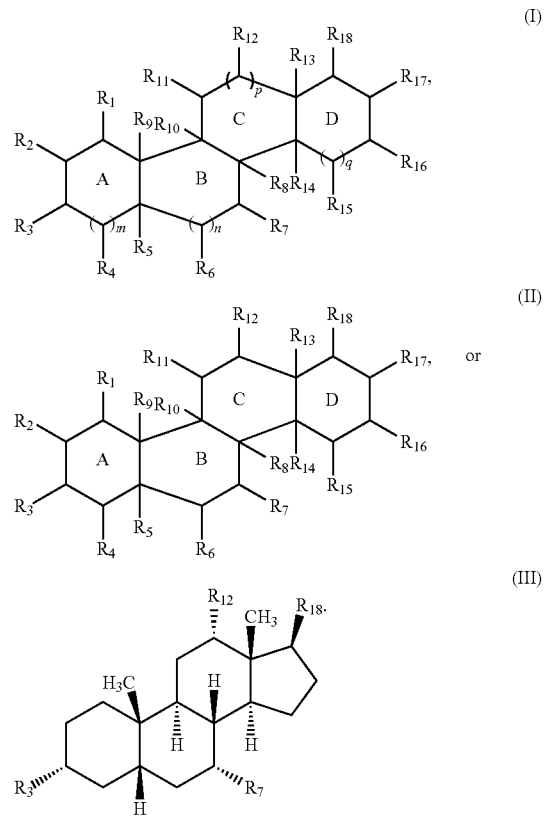

In embodiments, at least one of at least one of $R_1$-$R_{18}$, preferably at least one of $R_3$, $R_7$ and $R_{12}$, can have the following urethanyl structure:

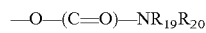

—O—(C=O)—NR$_{19}$R$_{20}$ where $R_{19}$ and $R_{20}$ are independently selected from hydrogen, substituted or unsubstituted alkyl, substituted or unsubstituted alkenyl, substituted or unsubstituted alkynyl, substituted or unsubstituted aryl, substituted or unsubstituted aminoalkyl, substituted or unsubstituted aminoalkenyl, substituted or unsubstituted aminoalkynyl, and substituted or unsubstituted aminoaryl, provided that at least one of $R_{19}$ and $R_{20}$ includes an amino group. In embodiments, $R_{19}$ is hydrogen and $R_{20}$ is substituted or unsubstituted ($C_2$-$C_6$) aminoalkyl.

In embodiments, $R_{18}$ can have the following structure:

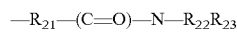

—R$_{21}$—(C=O)—N—R$_{22}$R$_{23}$ wherein $R_{21}$ is omitted or is selected from substituted or unsubstituted alkyl, substituted or unsubstituted alkenyl, substituted or unsubstituted alkynyl, and substituted or unsubstituted aryl, and $R_{22}$ and $R_{23}$ are independently selected from hydrogen, substituted or unsubstituted alkyl, substituted or unsubstituted alkenyl, substituted or unsubstituted alkynyl, and substituted or unsubstituted aryl, provided that at least one of $R_{22}$ and $R_{23}$ is not hydrogen.

When the CSA compound has a structure of Formula I, m, n, p, and q are independently 0 or 1.

When the CSA compound has a structure of Formula I or II, rings A, B, C, and D are independently saturated, or are fully or partially unsaturated, provided that at least two of rings A, B, C, and D are saturated.

When the CSA compound has a structure of Formula I or II, $R_1$ through $R_{18}$ are independently selected from the group consisting of hydrogen, hydroxyl, alkyl, hydroxyalkyl, alkyloxyalkyl, alkylcarboxyalkyl, alkylaminoalkyl, alkylaminoalkylamino, alkylaminoalkylaminoalkylamino, aminoalkyl, aryl, arylaminoalkyl, haloalkyl, alkenyl, alkynyl, oxo, linking group attached to a second steroid, aminoalkylurethanyl, aminoalkenylurethanyl, aminoalkynylurethanyl, aminoarylurethanyl, aminoalkyloxy, aminoalkylcarboxy, aminoalkyloxyalkyl, aminoalkylaminocarbonyl, aminoalkylcarboxamido, di(alkyl)aminoalkyl, $H_2N-HC(Q_5)-(C=O)-O-$, $H_2N-HC(Q_5)-(C=O)-NH-$, azidoalkyloxy, cyanoalkyloxy, $P.G.-HN-HC(Q_5)-(C=O)-O-$, guanidino-alkyloxy, quaternary ammonium alkylcarboxy, and guanidinoalkyl carboxy, where $Q_5$ is a side chain of any amino acid (including a side chain of glycine, i.e., H), and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, provided that at least one of $R_1$ through $R_4$, $R_6$, $R_7$, $R_{11}$, $R_{12}$, $R_{15}$, $R_{16}$, and $R_{18}$, and preferably at least one of $R_3$, $R_7$ and $R_{12}$, are independently selected from the group consisting of aminoalkylurethanyl, aminoalkenylurethanyl, aminoalkynylurethanyl, and aminoarylurethanyl.

In embodiments, $R_1$ through $R_{18}$ are independently selected from the group consisting of hydrogen, hydroxyl, substituted or unsubstituted ($C_1$-$C_{22}$)alkyl, substituted or unsubstituted ($C_1$-$C_{22}$)hydroxyalkyl, substituted or unsubstituted ($C_1$-$C_{22}$)alkyloxy-($C_1$-$C_{22}$)alkyl, substituted or unsubstituted ($C_1$-$C_{22}$)alkylcarboxy-($C_1$-$C_{22}$)alkyl, substituted or unsubstituted ($C_1$-$C_{22}$)alkylamino-($C_1$-$C_{22}$)alkyl, substituted or unsubstituted ($C_1$-$C_{22}$)alkylamino-($C_1$-$C_{22}$)alkylamino, substituted or unsubstituted ($C_1$-$C_{22}$)alkylamino-($C_1$-$C_{22}$)alkylamino-($C_1$-$C_{22}$)alkylamino, substituted or unsubstituted ($C_1$-$C_{22}$)aminoalkyl, substituted or unsubstituted aryl, substituted or unsubstituted arylamino-($C_1$-$C_{22}$)alkyl, substituted or unsubstituted ($C_1$-$C_{22}$)haloalkyl, substituted or unsubstituted ($C_2$-$C_6$)alkenyl, substituted or unsubstituted ($C_2$-$C_6$)alkynyl, oxo, linking group attached to a second steroid, substituted or unsubstituted ($C_1$-$C_{22}$) aminoalkylurethanyl, substituted or unsubstituted ($C_2$-$C_{22}$) aminoalkenylurethanyl, substituted or unsubstituted ($C_2$-$C_{22}$)aminoalkynylurethanyl, and substituted or unsubstituted aminoarylurethanyl, substituted or unsubstituted ($C_1$-$C_{22}$)aminoalkyloxy, substituted or unsubstituted ($C_1$-$C_{22}$)aminoalkylcarboxy, substituted or unsubstituted ($C_1$-$C_{22}$)aminoalkyloxy-($C_1$-$C_{22}$)alkyl, substituted or unsubstituted ($C_1$-$C_{22}$)aminoalkyl-aminocarbonyl, substituted or unsubstituted ($C_1$-$C_{22}$)aminoalkylcarboxamido, substituted or unsubstituted di($C_1$-$C_{22}$)alkylamino-($C_1$-$C_{22}$) alkyl, $H_2N-HC(Q_5)-(C=O)-O-$, $H_2N-HC(Q_5)-(C=O)-NH-$, substituted or unsubstituted ($C_1$-$C_{22}$)azidoalkyloxy, substituted or unsubstituted ($C_1$-$C_{22}$) cyanoalkyloxy, $P.G.-HN-HC(Q_5)-(C=O)-O-$, substituted or unsubstituted ($C_1$-$C_{22}$)guanidinoalkyloxy, substituted or unsubstituted ($C_1$-$C_{22}$)quaternary ammoniumalkyl carboxy, and substituted or unsubstituted ($C_1$-$C_{22}$) guanidinoalkyl carboxy, where $Q_5$ is a side chain of an amino acid (including a side chain of glycine, i.e., H), and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, provided that at least one of $R_1$ through $R_4$, $R_6$, $R_7$, $R_{11}$, $R_{12}$, $R_{15}$, $R_{16}$, and $R_{18}$, and preferably at least one of $R_3$, $R_7$ and $R_{12}$, are independently selected from the group consisting of substituted or unsubstituted ($C_1$-$C_{22}$)aminoalkylurethanyl, substituted or unsubstituted ($C_2$-$C_{22}$)aminoalkenylurethanyl, substituted or unsubstituted ($C_2$-$C_{22}$)aminoalkynylurethanyl, and substituted or unsubstituted aminoarylurethanyl.

In embodiments, $R_1$, $R_2$, $R_4$, $R_5$, $R_6$, $R_8$, $R_9$, $R_{10}$, $R_{11}$, $R_{13}$, $R_{14}$, $R_{15}$, $R_{16}$, and $R_{17}$ are independently selected from the group consisting of hydrogen and unsubstituted ($C_1$-$C_6$) alkyl.

In embodiments, $R_1$, $R_2$, $R_4$, $R_5$, $R_6$, $R_8$, $R_{10}$, $R_{11}$, $R_{14}$, $R_{16}$, and $R_{17}$ are each hydrogen and $R_9$ and $R_{13}$ are each methyl.

In embodiments, one or more of rings A, B, C, and D are heterocyclic.

In embodiments, rings A, B, C, and D are non-heterocyclic.

In embodiments, the CSA compound is a compound of Formula III, which is a subgenus of Formula I and Formula II with specified stereochemistry, wherein $R_1$, $R_2$, $R_4$, $R_5$, $R_6$, $R_8$, $R_{10}$, $R_{11}$, $R_{14}$, and $R_{16}$, are hydrogen or methyl as shown, and $R_{17}$ is omitted:

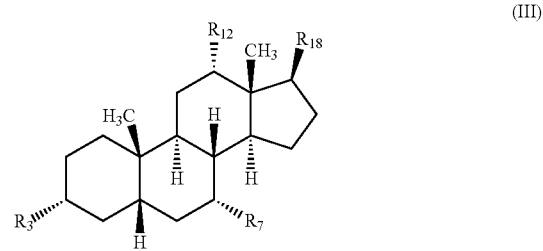

(III)

where $R_3$, $R_7$, $R_{12}$, and $R_{18}$ are as defined above for Formula I and II.

In embodiments, at least one, preferably at least two, more preferably all three, of $R_3$, $R_7$ and $R_{12}$ has the following urethanyl structure:

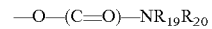

where $R_{19}$ and $R_{20}$ are independently selected from the group consisting of hydrogen, alkyl, alkenyl, alkynyl, aryl, aminoalkyl, aminoalkenyl, aminoalkynyl, or aminoaryl, provided that at least one of $R_{19}$ and $R_{20}$ includes an amino group. Preferably $R_{19}$ is hydrogen and $R_{20}$ is ($C_2$-$C_6$)aminoalkyl.

In embodiments, $R_{18}$ has the following structure:

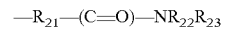

where, $R_{21}$ is omitted or is selected from substituted or unsubstituted alkyl, substituted or unsubstituted alkenyl, substituted or unsubstituted alkynyl, and substituted or unsubstituted aryl, such as substituted or unsubstituted ($C_1$-$C_{10}$)alkyl, substituted or unsubstituted ($C_2$-$C_{10}$) alkenyl, substituted or unsubstituted ($C_2$-$C_{10}$)alkynyl, or substituted or unsubstituted ($C_6$ or $C_{10}$)aryl, and $R_{22}$ and $R_{23}$ are independently selected from hydrogen, substituted or unsubstituted alkyl, substituted or unsub stituted alkenyl, substituted or unsubstituted alkynyl, and substituted or unsubstituted aryl, such as where $R_{22}$ and $R_{23}$ are independently selected from hydrogen, substituted or unsubstituted $(C_1-C_{24})$alkyl, substituted or unsubstituted $(C_2-C_{24})$alkenyl, substituted or unsubstituted $(C_2-C_{24})$alkynyl, substituted or unsubstituted $(C_6$ or $C_{10})$aryl, substituted or unsubstituted 5 to 10 membered heteroaryl, substituted or unsubstituted 5 to 10 membered heterocyclyl, substituted or unsubstituted $(C_7-C_{13})$aralkyl, substituted or unsubstituted 5 to 10 membered heteroaryl-$(C_1-C_6)$alkyl, substituted or unsubstituted $(C_3-C_{10})$carbocyclyl, substituted or unsubstituted $(C_4-C_{10})$carbocyclylalkyl, and 5 to 10 membered heterocyclyl-$(C_1-C_6)$alkyl, provided that at least one of $R_{21}$ and $R_{22}$ is not hydrogen. In some embodiments, $R_{22}$ and $R_{23}$ together with the atoms to which they are attached, form an optionally substituted 4 to 10 membered cyclic alkyl ring or 5 to 10 membered heterocyclic ring.

In embodiments, where one or two of $R_3$, $R_7$, and $R_{12}$ independently has a urethanyl structure as defined herein, one or two of $R_3$, $R_7$, and $R_{12}$ are independently selected from the group consisting of hydrogen, $(C_1-C_{22})$alkyl, $(C_1-C_{22})$hydroxyalkyl, $(C_1-C_{22})$alkyloxy-$(C_1-C_{22})$alkyl, $(C_1-C_{22})$alkylcarboxy-$(C_1-C_{22})$alkyl, $(C_1-C_{22})$alkylamino-$(C_1-C_{22})$alkyl, $(C_1-C_{22})$alkylamino-$(C_1-C_{22})$alkylamino, $(C_1-C_{22})$alkylamino-$(C_1-C_{22})$alkylamino-$(C_1-C_{18})$alkylamino, $(C_1-C_{22})$aminoalkyl, arylamino-$(C_1-C_{22})$alkyl, $(C_1-C_{22})$aminoalkyloxy, $(C_1-C_{22})$aminoalkyl-carboxy, $(C_1-C_{22})$aminoalkyloxy-$(C_1-C_{22})$alkyl, $(C_1-C_{22})$aminoalkyl-aminocarbonyl, $(C_1-C_{22})$aminoalkylcarboxamido, di$(C_1-C_{22})$alkylaminoalkyl, $(C_1-C_{22})$guanidinoalkyloxy, $(C_1-C_{22})$quaternary ammonium alkylcarboxy, and $(C_1-C_{22})$guanidinoalkyl carboxy.

Preferably, where one or two of $R_3$, $R_7$, and $R_{12}$ independently has a urethanyl structure as defined herein, one or two of $R_3$, $R_7$, and $R_{12}$ are independently selected from the group consisting of hydrogen, $(C_1-C_6)$alkyl, $(C_1-C_6)$hydroxyalkyl, $(C_1-C_{16})$alkyloxy-$(C_1-C_5)$alkyl, $(C_1-C_{16})$alkylcarboxy-$(C_1-C_5)$alkyl, $(C_1-C_{16})$alkylamino-$(C_1-C_5)$alkyl, $(C_1-C_{16})$alkylamino-$(C_1-C_5)$alkylamino, $(C_1-C_{16})$alkylamino-$(C_1-C_{16})$alkylamino-$(C_1-C_5)$alkylamino, $(C_1-C_6)$ aminoalkyl, arylamino-$(C_1-C_5)$alkyl, $(C_1-C_5)$aminoalkyloxy, $(C_1-C_{16})$aminoalkyloxy-$(C_1-C_5)$alkyl, $(C_1-C_5)$aminoalkylcarboxy, $(C_1-C_5)$aminoalkylaminocarbonyl, $(C_1-C_5)$aminoalkyl-carboxamido, di$(C_1-C_5)$alkylamino-$(C_1-C_5)$alkyl, $(C_1-C_5)$guanidinoalkyloxy, $(C_1-C_{16})$quaternary ammonium alkylcarboxy, and $(C_1-C_{16})$guanidinoalkylcarboxy.

In some embodiments, $R_3$, $R_7$, and $R_{12}$ are the same urethanyl group.

In some embodiments, one or two of $R_3$, $R_7$, and $R_{12}$ are aminoalkyloxy.

In some embodiments, one or two of $R_3$, $R_7$, and $R_{12}$ are aminoalkylcarboxy.

Non-limiting examples of CSA compounds in which at least one of $R_3$, $R_7$ and $R_{12}$ is attached to the steroidal backbone by a urethane linkage are CSA-255, CSA-256, CSA-257, and salts thereof:

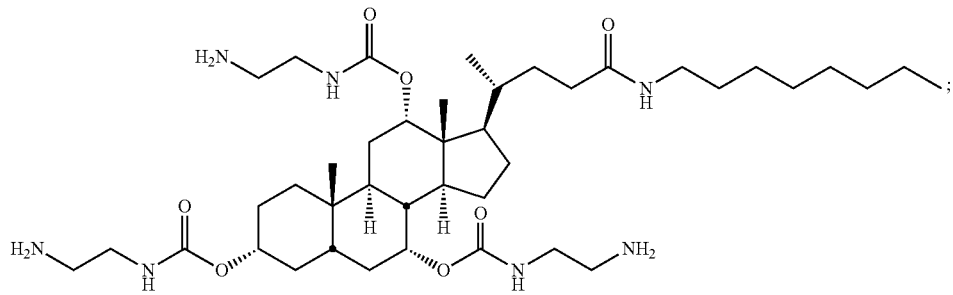

(CSA-255)

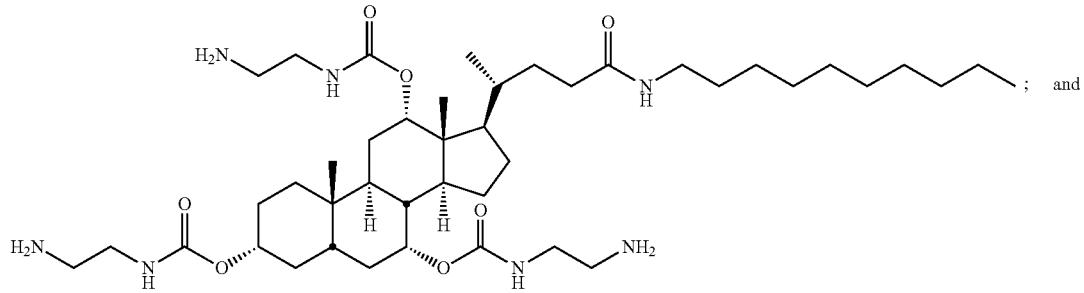

(CSA-256)

; and

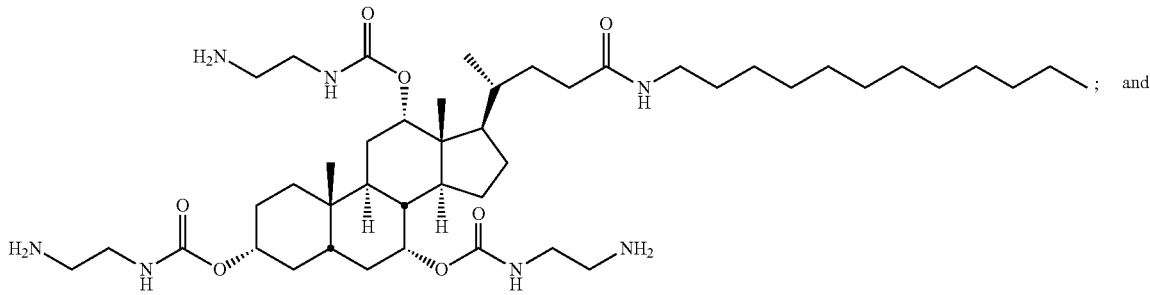
(CSA-257)

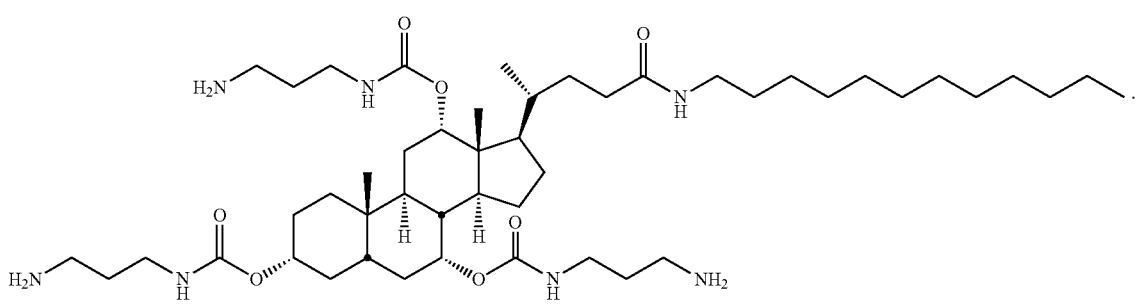
(CSA-258)

Pharmaceutical Compositions

While CSA compounds described herein can be administered alone, it may be preferable to formulate the compounds as pharmaceutical compositions (i.e., formulations). A pharmaceutical composition is any composition that may be administered in vitro or in vivo or both to a subject in order to treat or ameliorate a condition. In a preferred embodiment, a pharmaceutical composition may be administered in vivo. A subject may include one or more cells or tissues, or organisms. In exemplary embodiments, the subject is an animal. In embodiments, the animal is a mammal. The mammal may be a human or primate in some embodiments. A mammal includes any mammal, such as by way of non-limiting example, cattle, pigs, sheep, goats, horses, camels, buffalo, cats, dogs, rats, mice, and humans.

"Pharmaceutically acceptable" and "physiologically acceptable" mean a biologically compatible formulation, gaseous, liquid or solid, or mixture thereof, which is suitable for one or more routes of administration, in vivo delivery, or contact. A formulation is compatible in that it does not destroy activity of an active ingredient therein (e.g., a CSA compound), or induce adverse side effects that far outweigh any prophylactic or therapeutic effect or benefit.

Pharmaceutical compositions may be formulated with a pharmaceutically acceptable excipient, such as a carrier, solvent, stabilizer, adjuvant, diluent, etc., depending upon the particular mode of administration and dosage form. The pharmaceutical compositions can be formulated to achieve a physiologically compatible pH, and may range from about 3 to 11, preferably about 3 to 7, depending on the formulation and route of administration. In alternative embodiments, the pH is adjusted to about 5 to 8. The pharmaceutical compositions may comprise a therapeutically or prophylactically effective amount of at least one compound as described herein, together with one or more pharmaceutically acceptable excipients.

The pharmaceutical composition may comprise a combination of compounds described herein and/or may include a second active ingredient useful in the treatment or prevention of bacterial infection (e.g., anti-bacterial or anti-microbial agents).

The composition can be formulated as a coating, such as on a medical device. In embodiments, the coating is on a medical instrument.

Formulations for parenteral or oral administration can be solids, liquid solutions, emulsions or suspensions. Inhalable formulations for pulmonary administration can be liquids or powders. A pharmaceutical composition can be formulated as a lyophilized solid that is reconstituted with a physiologically compatible solvent prior to administration. Alternative pharmaceutical compositions may be formulated as syrups, creams, ointments, tablets, etc.

Compositions may contain one or more excipients. Pharmaceutically acceptable excipients are determined in part by the particular composition being administered as well as by the particular method used to administer the composition. There exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are pharmaceutically acceptable excipients.

Pharmaceutical compositions may be formulated in any form suitable for the intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as cross-linked povidone, maize starch, or alginic acid; binding agents, such as povidone, starch, gelatin or acacia; and lubricating agents, such as magnesium stearate, stearic acid or talc.

Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

Pharmaceutical compositions can be formulated as a suspension comprising a CSA compound in admixture with at least one pharmaceutically acceptable excipient suitable for the manufacture of a suspension.

Pharmaceutical compositions can be formulated as dispersible powders and granules suitable for preparation of a suspension by the addition of suitable excipients.

Excipients suitable for use in connection with suspensions include suspending agents, such as sodium carboxymethylcellulose, methylcellulose, hydroxypropyl methylcellulose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); polysaccharides and polysaccharide-like compounds (e.g. dextran sulfate); glycoaminoglycans and glycosaminoglycan-like compounds (e.g., hyaluronic acid); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

Pharmaceutical compositions may be in the form of oil-in water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Pharmaceutical compositions may be in the form of a sterile injectable preparation, such as a sterile injectable aqueous emulsion or oleaginous suspension. The emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propandiol.

Sterile injectable preparations may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose, any bland fixed oil may be employed including synthetic mono- or diglycerides. In addition, fatty acids such as oleic acid may likewise be used in the preparation of injectables.

To obtain a stable water-soluble dose form of a pharmaceutical composition, a pharmaceutically acceptable salt of a compound described herein may be dissolved in an aqueous solution of an organic or inorganic acid, such as 0.3 M solution of succinic acid, or more preferably, citric acid. If a soluble salt form is not available, the compound may be dissolved in a suitable co-solvent or combination of co-solvents. Examples of suitable co-solvents include alcohol, propylene glycol, polyethylene glycol 300, polysorbate 80, glycerin and the like in concentrations ranging from about 0 to 60% of the total volume. In one embodiment, the active compound is dissolved in DMSO and diluted with water.

Pharmaceutical composition may also be in the form of a solution of a salt form of the active ingredient in an appropriate aqueous vehicle, such as water or isotonic saline or dextrose solution. Also contemplated are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, and complexation.

Many therapeutics have undesirably short half-lives and/or undesirable toxicity. Thus, the concept of improving half-life or toxicity is applicable to various treatments and fields. Pharmaceutical compositions can be prepared, however, by complexing the therapeutic with a biochemical moiety to improve such undesirable properties. Proteins are a particular biochemical moiety that may be complexed with a CSA for administration in a wide variety of applications. In some embodiments, one or more CSAs are complexed with a protein. In some embodiments, one or more CSAs are complexed with a protein to increase the CSA's half-life. In other embodiments, one or more CSAs are complexed with a protein to decrease the CSA's toxicity. Albumin is a particularly preferred protein for complexation with a CSA. In some embodiments, the albumin is fat-free albumin.

With respect to the CSA therapeutic, the biochemical moiety for complexation can be added to the pharmaceutical composition as 0.25, 0.5, 0.75, 1, 1.5, 2, 2.5, 3, 3.5, 4, 4.5, 5, 10, 20, 50, or 100 weight equivalents, or a range bounded by any two of the aforementioned numbers, or about any of the numbers. In embodiments, the weight ratio of albumin to CSA is about 18:1 or less, such as about 9:1 or less. In embodiments, the CSA is coated with albumin.

Non-biochemical compounds can be added to the pharmaceutical compositions to reduce the toxicity of the therapeutic and/or improve the half-life. Suitable amounts and ratios of an additive that can reduce toxicity can be determined via a cellular assay. With respect to the CSA therapeutic, toxicity reducing compounds can be added to the pharmaceutical composition as 0.25, 0.5, 0.75, 1, 1.5, 2, 2.5, 3, 3.5, 4, 4.5, 5, 10, 20, 50, or 100 weight equivalents, or a range bounded by any two of the aforementioned numbers, or about any of the numbers. In embodiments, the toxicity reducing compound is a cocoamphodiacetate such as Miranol® (disodium cocoamphodiacetate). In embodiments, the toxicity reducing compound is an amphoteric surfactant. In embodiments, the toxicity reducing compound is a surfactant. In embodiments, the molar ratio of cocoamphodiacetate to CSA is between about 8:1 and 1:1, preferably about 4:1. In embodiments, the toxicity reducing compound is allantoin.

In embodiments, a CSA composition is prepared utilizing one or more surfactants. In specific embodiments, the CSA is complexed with one or more poloxamer surfactants. Poloxamer surfactants are nonionic triblock copolymers composed of a central hydrophobic chain of polyoxypropylene (poly(propylene oxide)) flanked by two hydrophilic chains of polyoxyethylene (poly(ethylene oxide)). In some embodiments, the poloxamer is a liquid, paste, or flake (solid). Examples of suitable poloxamers include those by the trade names Synperonics, Pluronics, or Kolliphor. In some embodiments, one or more of the poloxamer surfactant in the composition is a flake poloxamer. In embodiments, the one or more poloxamer surfactant in the composition has a molecular weight of about 3600 g/mol for the central hydrophobic chain of polyoxypropylene and has about 70% polyoxyethylene content. In embodiments, the ratio of the one or more poloxamer to CSA is between about 50 to 1; about 40 to 1; about 30 to 1; about 20 to 1; about 10 to 1; about 5 to 1; about 1 to 1; about 1 to 10; about 1 to 20; about 1 to 30; about 1 to 40; or about 1 to 50. In embodiments, the ratio of the one or more poloxamer to CSA is between 50 to 1; 40 to 1; 30 to 1; 20 to 1; 10 to 1; 5 to 1; 1 to 1; 1 to 10; 1 to 20; 1 to 30; 1 to 40; or 1 to 50. In embodiments, the ratio of the one or more poloxamer to CSA is between about 50 to 1 to about 1 to 50. In embodiments, the ratio of the one or more poloxamer to CSA is between about 30 to 1 to about 3 to 1. In some embodiments, the poloxamer is Pluronic F127.

The amount of poloxamer may be based upon a weight percentage of the composition. In embodiments, the amount of poloxamer is about 10%, 15%, 20%, 25%, 30%, 35%, 40%, about any of the aforementioned numbers, or a range bounded by any two of the aforementioned numbers or the formulation. In embodiments, the one or more poloxamer is between about 10% to about 40% by weight of a formulation administered to the patient. In some embodiments, the one or more poloxamer is between about 20% to about 30% by weight of the formulation. In embodiments, the formulation contains less than about 50%, 40%, 30%, 20%, 10%, 5%, or 1% of CSA. In embodiments, the formulation contains less than about 20% by weight of CSA. The above described poloxamer formulations are particularly suited for the methods of treatment, device coatings, preparation of unit dosage forms (i.e., solutions, mouthwashes, injectables), etc.

In embodiments, the compounds described herein may be formulated for oral administration in a lipid-based formulation suitable for low solubility compounds. Lipid-based formulations can generally enhance the oral bioavailability of such compounds.

A pharmaceutical composition may comprise a therapeutically or prophylactically effective amount of a compound described herein, together with at least one pharmaceutically acceptable excipient selected from the group consisting of medium chain fatty acids or propylene glycol esters thereof (e.g., propylene glycol esters of edible fatty acids such as caprylic and capric fatty acids) and pharmaceutically acceptable surfactants such as polyoxyl 40 hydrogenated castor oil.

In embodiments, cyclodextrins may be added as aqueous solubility enhancers. Preferred cyclodextrins include hydroxypropyl, hydroxyethyl, glucosyl, maltosyl and maltotriosyl derivatives of α-, β-, and γ-cyclodextrin. A particularly preferred cyclodextrin solubility enhancer is hydroxypropyl-o-cyclodextrin (BPBC), which may be added to any of the above-described compositions to further improve the aqueous solubility characteristics of the compounds of the embodiments. In one embodiment, the composition comprises about 0.1% to about 20% hydroxypropyl-o-cyclodextrin, more preferably about 1% to about 15% hydroxypropyl-o-cyclodextrin, and even more preferably from about 2.5% to about 10% hydroxypropyl-o-cyclodextrin. The amount of solubility enhancer employed will depend on the amount of the compound of the embodiments in the composition.

Synthesis

The methods disclosed herein may be as described below, or by modification of these methods. Ways of modifying the methodology include, among others, temperature, solvent, reagents etc., known to those skilled in the art. In general, during any of the processes for preparation disclosed herein, it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and P. G. M. Green, T. W. Wutts, *Protecting Groups in Organic Synthesis* (3rd ed.) Wiley, New York (1999), which are both hereby incorporated herein by reference in their entirety. The protecting groups may be removed at a convenient subsequent stage using methods known from the art. Synthetic chemistry transformations useful in synthesizing applicable compounds are known in the art and include e.g. those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

An exemplary but non-limiting general synthetic scheme for preparing compounds of Formula I, Formula II, and Formula III is shown in Scheme A. Unless otherwise indicated, the variable definitions are as above for Formulae I, II and/or III.

Scheme A

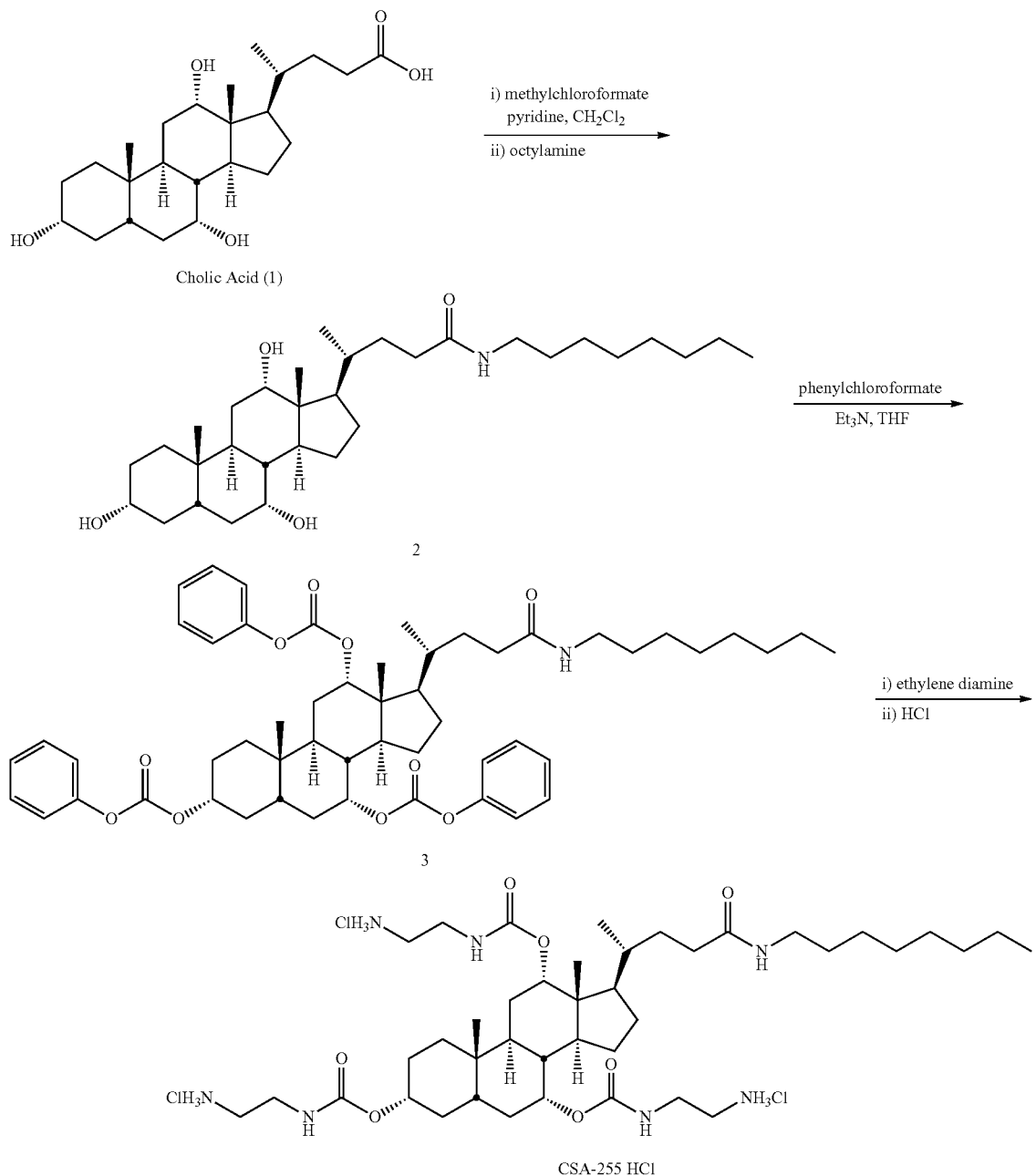

Cholic acid (1) is treated with methylchloroformate in pyridine and dichloromethane to form an intermediate with an acid anhydride at the C24 position, followed by treatment with a primary or secondary amine $R_{22}R_{23}NH$ (e.g., octylamine) to yield intermediate compound (2), or analog thereof, having an amide at the C24 position. The amide may optionally be modified, and optionally protected, before or after any of the next steps, to yield a desired functional group at the $R_{18}$ position. Intermediate compound (2), or analog thereof, is treated with R-chloroformate (e.g., phenylchloroformate) in the presence of triethylamine and tetrahydrofuran to yield intermediate compound (3), or analog thereof, having a carbonate at the C3, C7 and C12 positions. Intermediate compound (3), or analog thereof, is treated with an alkylene or arylene diamine (e.g., excess ethylene diamine), followed by acidification with hydrochloric acid to form the acid addition salt of the CSA compound (e.g., CSA-255 HCl).

In some embodiments, some or all of the foregoing steps can be performed in a one-pot reaction without purification of intermediate compounds.

In some embodiments, the intermediate formed by reacting intermediate compound (3), or analog thereof, is treated with Tris-Boc to protect the amino groups, followed by purification, followed by treatment with HCl in dioxane to deprotect the amine and form the HCl acid addition salt.

The foregoing reactions can be modified to use decylamine or dodecylamine when forming intermediate compound (2) in order to yield CSA-256 HCl or CSA-257 HCl.

The HCl acid addition CSA salt can be purified and optionally neutralized with a base, followed by separation (e.g., 2-phase liquid extraction followed by evaporation of organic solvent) to yield the purified free base. The free base can be used as is or it can be acidified with any desired acid to form an acid addition salt.

An example acid addition salt is the salt of 1,5-naphthalenedisulonic acid (1,5-NDSA salt, e.g., di-addition salt), which is highly insoluble and is therefore useful as a coating, such as a coating on an implantable medical device. In some cases, the NDSA salt is milled to submicron sized particles and put in a coating in particulate form. The NDSA salt does not dissolve in ethyelene oxide, which is commonly used to sterilize medical devices, and therefore can remains as a stable coating after multiple sterilization cycles.

Making the CSA compound ionic, such as by exchanging the NDSA portion with other anions, e.g., chloride ions using HCl, sodium chloride, etc., results in first order release kinetics, which can be accelerated in acidic conditions.

An advantage of the disclosed CSA compounds is that they are thermally stable and will not form polymerized or cross-linked urethanes even at high temperature.

EXAMPLES

The antimicrobial activity of CSA-255 was determined in comparison to CSA-44, a CSA compound known to have very high antimicrobial activity compared to other CSAs. The microbes used in the comparative test was were methicillin resistant Staphylococcus aureus (MRSA) BAA-41 and Pseudomonas aeruginosa (PA01 47085). The measured minimum inhibitory concentrations (MICs) are set forth in Table 1.

TABLE 1

| CSA | Pathogen | MIC |
|---|---|---|
| 44 | MRSA BAA-41 | 2 µg/ml |
|  | PA01 47085 | 2 µg/ml |
| 255 | MRSA BAA-41 | 4 µg/ml |
|  | PA01 47085 | 2 µg/ml |

It was unexpected that CSA compounds within the scope of the invention have antimicrobial activities the same or similar to CSAs that have been known and used for years but with substantially different linkages of the active amino groups to the sterol backbone.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A cationic steroidal antimicrobial (CSA) compound having a structure of Formula II, or a salt thereof:

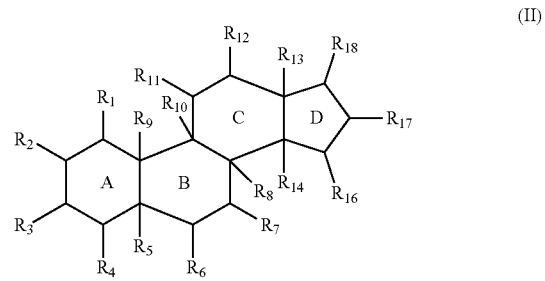

(II)

where,
rings A, B, C, and D are saturated; and
$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{16}$, $R_{17}$, and $R_{18}$ are independently selected from the group consisting of hydrogen, hydroxyl, alkyl, hydroxyalkyl, alkyloxyalkyl, alkylcarboxyalkyl, alkylaminoalkyl, alkylaminoalkylamino, alkylaminoalkylaminoalkylamino, aminoalkyl, aryl, arylaminoalkyl, haloalkyl, alkenyl, alkynyl, oxo, linking group attached to a second steroid, aminoalkylurethanyl, aminoalkenylurethanyl, aminoalkynylurethanyl, aminoarylurethanyl, aminoalkyloxy, aminoalkylcarboxy, aminoalkyloxyalkyl, aminoalkylaminocarbonyl, aminoalkylcarboxamido, di(alkyl)aminoalkyl, $H_2N-HC(Q_5)-(C=O)-O-$, $H_2N-HC(Q_5)-(C=O)-NH-$, azidoalkyloxy, cyanoalkyloxy, P.G.-HN-HC($Q_5$)-(C=O)-O-, guanidino-alkyloxy, quaternary ammonium alkylcarboxy, and guanidinoalkyl carboxy, where $Q_5$ is a side chain of an amino acid and P.G. is an amino protecting group,
provided that at least three of $R_1$, $R_2$, $R_3$, $R_4$, $R_6$, $R_7$, $R_{11}$, $R_{12}$, $R_{16}$, and $R_{18}$ are independently selected from the group consisting of aminoalkylurethanyl, aminoalkenylurethanyl, aminoalkynylurethanyl, and aminoarylurethanyl.

2. The CSA compound of claim 1, wherein at least two of $R_3$, $R_7$ and $R_{12}$ are independently selected from the group consisting of aminoalkylurethanyl, aminoalkenylurethanyl, aminoalkynylurethanyl, and aminoarylurethanyl.

3. The CSA compound of claim 1, wherein:
$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{16}$, $R_{17}$, and $R_{18}$ are independently selected from the group consisting of hydrogen, hydroxyl, substituted or unsubstituted ($C_1$-$C_{22}$)alkyl, substituted or unsubstituted ($C_1$-$C_{22}$)hydroxyalkyl, substituted or unsubstituted ($C_1$-$C_{22}$)alkyloxy-($C_1$-$C_{22}$)alkyl, substituted or unsubstituted ($C_1$-$C_{22}$)alkylcarboxy-($C_1$-$C_{22}$)alkyl, substituted or unsubstituted ($C_1$-$C_{22}$)alkylamino-($C_1$-$C_{22}$)alkyl, substituted or unsubstituted ($C_1$-$C_{22}$)alkylamino-($C_1$-$C_{22}$)alkylamino, substituted or unsubstituted ($C_1$-$C_{22}$)alkylamino-($C_1$-$C_{22}$)alkylamino-($C_1$-$C_{22}$)alkylamino, substituted or unsubstituted ($C_1$-$C_{22}$) aminoalkyl, substituted or unsubstituted aryl, substituted or unsubstituted arylamino-($C_1$-$C_{22}$)alkyl, substituted or unsubstituted ($C_1$-$C_{22}$)haloalkyl, substituted or unsubstituted ($C_2$-$C_6$)alkenyl, substituted or unsubstituted ($C_2$-$C_6$)alkynyl, oxo, linking group attached to a second steroid, substituted or unsubstituted ($C_1$-$C_{22}$)aminoalkylurethanyl, substituted or unsubstituted ($C_2$-$C_{22}$)aminoalkenylurethanyl, substituted or unsubstituted ($C_2$-$C_{22}$)aminoalkynylurethanyl, and substituted or unsubstituted aminoarylurethanyl, substituted or unsubstituted ($C_1$-$C_{22}$)aminoalkyloxy, substituted or unsubstituted $(C_1-C_{22})$aminoalkylcarboxy, substituted or unsubstituted $(C_1-C_{22})$aminoalkyloxy-$(C_1-C_{22})$alkyl, substituted or unsubstituted $(C_1-C_{22})$aminoalkylamino-carbonyl, substituted or unsubstituted $(C_1-C_{22})$aminoalkylcarboxamido, substituted or unsubstituted di$(C_1-C_{22})$alkylamino-$(C_1-C_{22})$alkyl, $H_2N-HC(Q_5)-(C=O)-O-$, $H_2N-HC(Q_5)-(C=O)-NH-$, substituted or unsubstituted $(C_1-C_{22})$azidoalkyloxy, substituted or unsubstituted $(C_1-C_{22})$cyanoalkyloxy, $P.G.-HN-HC(Q_5)-(C=O)-O-$, substituted or unsubstituted $(C_1-C_{22})$guanidinoalkyloxy, substituted or unsubstituted $(C_1-C_{22})$quaternary ammoniumalkyl carboxy, and substituted or unsubstituted $(C_1-C_{22})$guanidinoalkyl carboxy, where $Q_5$ is a side chain of an amino acid and P.G. is an amino protecting group, provided that at least three of $R_1$, $R_2$, $R_3$, $R_4$, $R_6$, $R_7$, $R_{11}$, $R_{12}$, $R_{16}$, and $R_{18}$ are independently selected from the group consisting of substituted or unsubstituted $(C_1-C_{22})$aminoalkylurethanyl, substituted or unsubstituted $(C_2-C_{22})$aminoalkenylurethanyl, substituted or unsubstituted $(C_2-C_{22})$aminoalkynylurethanyl, and substituted or unsubstituted aminoarylurethanyl.

4. The CSA compound of claim 1, wherein at least two of $R_3$, $R_7$ and $R_{12}$ are independently selected from the group consisting of substituted or unsubstituted $(C_1-C_{22})$aminoalkylurethanyl, substituted or unsubstituted $(C_2-C_{22})$aminoalkenylurethanyl, substituted or unsubstituted $(C_2-C_{22})$aminoalkynylurethanyl, and substituted or unsubstituted aminoarylurethanyl.

5. The CSA compound of claim 1, wherein at least two of $R_3$, $R_7$ and $R_{12}$ have the following urethanyl structure:

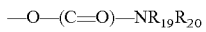
—O—(C=O)—NR₁₉R₂₀ where $R_{19}$ and $R_{20}$ are independently selected from hydrogen, substituted or unsubstituted alkyl, substituted or unsubstituted alkenyl, substituted or unsubstituted alkynyl, substituted or unsubstituted aryl, substituted or unsubstituted aminoalkyl, substituted or unsubstituted aminoalkenyl, substituted or unsubstituted aminoalkynyl, and substituted or unsubstituted aminoaryl, provided that at least one of $R_{19}$ and $R_{20}$ includes an amino group.

6. The CSA compound of claim 5, wherein $R_{19}$ is hydrogen and $R_{20}$ is substituted or unsubstituted $(C_2-C_6)$aminoalkyl.

7. The CSA compound of claim 1, wherein $R_{18}$ has the following structure:

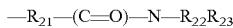
—R₂₁—(C=O)—N—R₂₂R₂₃ where,
R₂₁ is a bond or is selected from substituted or unsubstituted alkyl, substituted or unsubstituted alkenyl, substituted or unsubstituted alkynyl, and substituted or unsubstituted aryl, and R₂₂ and R₂₃ are independently selected from hydrogen, substituted or unsubstituted alkyl, substituted or unsubstituted alkenyl, substituted or unsubstituted alkynyl, and substituted or unsubstituted aryl, provided that at least one of R₂₂ and R₂₃ is not hydrogen.

8. The CSA compound of claim 7, wherein:
R₂₁ is a bond or is selected from substituted or unsubstituted $(C_1-C_{10})$alkyl, substituted or unsubstituted $(C_2-C_{10})$alkenyl, substituted or unsubstituted $(C_2-C_{10})$alkynyl, and substituted or unsubstituted $(C_6$ or $C_{10})$aryl, and R₂₂ and R₂₃ are independently selected from hydrogen, substituted or unsubstituted $(C_1-C_{24})$alkyl, substituted or unsubstituted $(C_2-C_{24})$alkenyl, substituted or unsubstituted $(C_2-C_{24})$alkynyl, and substituted or unsubstituted $(C_6$ or $C_{10})$aryl, provided that at least one of R₂₁ and R₂₂ is not hydrogen.

9. The CSA compound of claim 1, wherein:
two of $R_3$, $R_7$, and $R_{12}$ are independently selected from the group consisting of aminoalkylurethanyl, aminoalkenylurethanyl, aminoalkynylurethanyl, and aminoarylurethanyl, and one of $R_3$, $R_7$, and $R_{12}$ is selected from the group consisting of $(C_1-C_{22})$alkyl, $(C_1-C_{22})$hydroxyalkyl, $(C_1-C_{22})$alkyloxy-$(C_1-C_{22})$alkyl, $(C_1-C_{22})$alkylcarboxy-$(C_1-C_{22})$ alkyl, $(C_1-C_{22})$ alkylamino-$(C_1-C_{22})$alkyl, $(C_1-C_{22})$alkylamino-$(C_1-C_{22})$alkylamino, $(C_1-C_{22})$alkylamino-$(C_1-C_{22})$alkylamino-$(C_1-C_{18})$ alkylamino, $(C_1-C_{22})$amino-alkyl, arylamino-$(C_1-C_{22})$ alkyl, $(C_1-C_{22})$aminoalkyloxy, $(C_1-C_{22})$aminoalkylcarboxy, $(C_1-C_{22})$aminoalkyloxy-$(C_1-C_{22})$alkyl, $(C_1-C_{22})$aminoalkyl-aminocarbonyl, $(C_1-C_{22})$aminoalkylcarboxamido, di$(C_1-C_{22})$alkylaminoalkyl, $(C_1-C_{22})$guanidinoalkyloxy, $(C_1-C_{22})$quaternary ammonium alkylcarboxy, and $(C_1-C_{22})$ guanidinoalkyl carboxy.

10. The CSA compound of claim 9, wherein:
one of $R_3$, $R_7$, and $R_{12}$ is selected from the group consisting of $(C_1-C_6)$alkyl, $(C_1-C_6)$hydroxyalkyl, $(C_1-C_{16})$alkyloxy-$(C_1-C_5)$alkyl, $(C_1-C_{16})$alkylcarboxy-$(C_1-C_5)$alkyl, $(C_1-C_{16})$alkylamino-$(C_1-C_5)$alkyl, $(C_1-C_{16})$alkyl-amino-$(C_1-C_5)$alkylamino, $(C_1-C_{16})$alkylamino-$(C_1-C_{16})$alkylamino-$(C_1-C_5)$alkylamino, $(C_1-C_{16})$ aminoalkyl, arylamino-$(C_1-C_5)$alkyl, $(C_1-C_5)$aminoalkyloxy, $(C_1-C_{16})$aminoalkyloxy-$(C_1-C_5)$alkyl, $(C_1-C_5)$aminoalkylcarboxy, $(C_1-C_5)$aminoalkylaminocarbonyl, $(C_1-C_5)$aminoalkyl-carboxamido, di$(C_1-C_5)$alkylamino-$(C_1-C_5)$alkyl, $(C_1-C_5)$guanidinoalkyloxy, $(C_1-C_{16})$quaternary ammonium alkylcarboxy, and $(C_1-C_{16})$ guanidinoalkylcarboxy.

11. The CSA compound of claim 1, wherein $R_1$, $R_2$, $R_4$, $R_5$, $R_6$, $R_8$, $R_9$, $R_{10}$, $R_{11}$, $R_{13}$, $R_{14}$, $R_{16}$, and $R_{17}$ are independently selected from the group consisting of hydrogen and unsubstituted $(C_1-C_6)$ alkyl.

12. The CSA compound of claim 1, wherein $R_3$, $R_7$, and $R_{12}$ are the same urethanyl group.

13. The CSA compound of claim 1, wherein the CSA compound has a structure of Formula III:

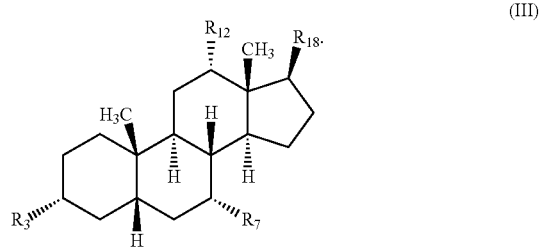

(III)

14. The CSA compound of claim 1, wherein the CSA compound is selected from CSA-255, CSA-256, CSA-257, CSA-258, and salts thereof:

(CSA-255)
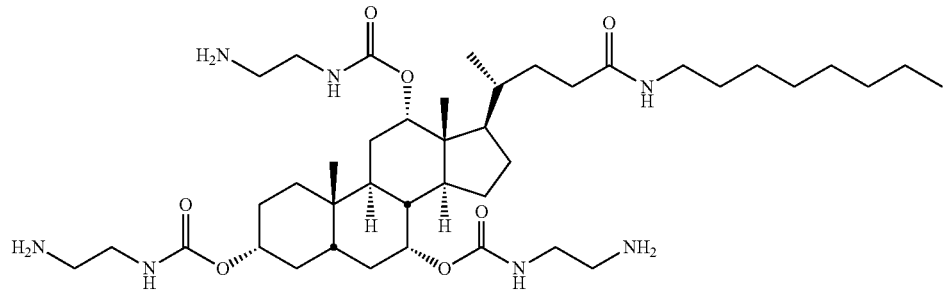
(CSA-256)
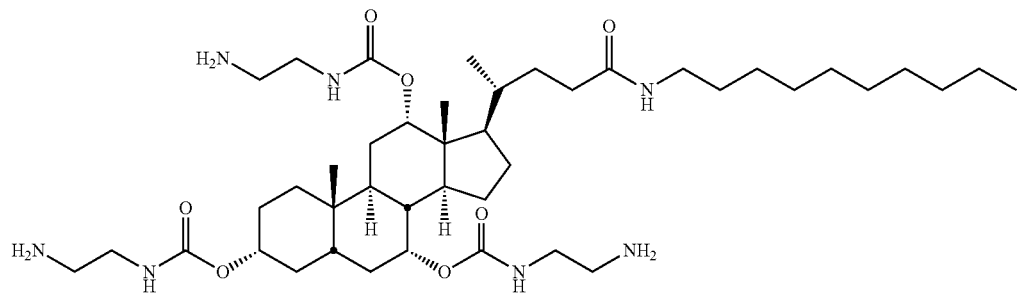
(CSA-257)
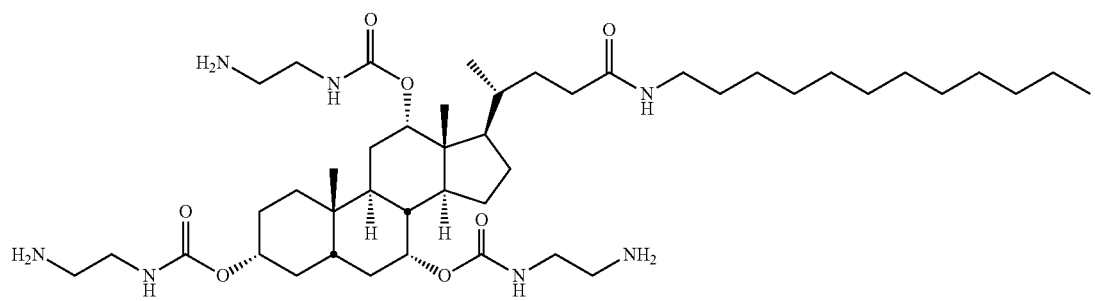
(CSA-258)
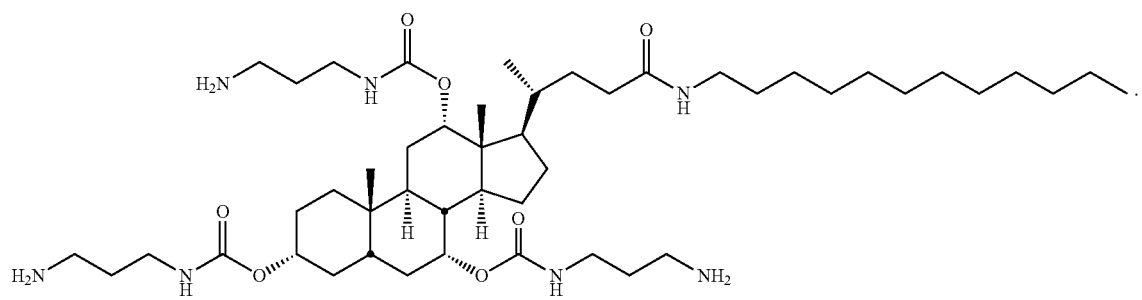

15. A pharmaceutical composition comprising a CSA compound of claim 1 and a pharmaceutically acceptable excipient selected from a carrier, solvent, stabilizer, adjuvant, and diluent.

16. A cationic steroidal antimicrobial (CSA) compound having a structure of Formula III, or a salt thereof:

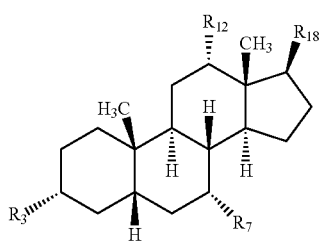

(III)

where,
- $R_3$, $R_7$, and $R_{12}$ are independently selected from the group consisting of aminoalkylurethanyl, aminoalkenylurethanyl, aminoalkynylurethanyl, and aminoarylurethanyl; and
- $R_{18}$ is selected from the group consisting of hydrogen, hydroxyl, alkyl, hydroxyalkyl, alkyloxyalkyl, alkylcarboxyalkyl, alkylaminoalkyl, alkylaminoalkylamino, alkylaminoalkylaminoalkylamino, aminoalkyl, aryl, arylaminoalkyl, haloalkyl, alkenyl, alkynyl, oxo, linking group attached to a second steroid, aminoalkylurethanyl, aminoalkenylurethanyl, aminoalkynylurethanyl, aminoarylurethanyl, aminoalkyloxy, aminoalkylcarboxy, aminoalkyloxyalkyl, aminoalkylaminocarbonyl, aminoalkylcarboxamido, di(alkyl)aminoalkyl, $H_2N$—$HC(Q_5)$-$(C{=}O)$—$O$—, $H_2N$—$HC(Q_5)$-$(C{=}O)$—$NH$—, azidoalkyloxy, cyanoalkyloxy, P.G.-$HN$—$HC(Q_5)$-$(C{=}O)$—$O$—, guanidino-alkyloxy, quaternary ammonium alkylcarboxy, and guanidinoalkyl carboxy, where $Q_5$ is a side chain of an amino acid and P.G. is an amino protecting group.

17. The CSA compound of claim 16, wherein $R_3$, $R_7$ and $R_{12}$ independently have the following urethanyl structure:

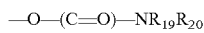

—O—(C=O)—$NR_{19}R_{20}$ where $R_{19}$ and $R_{20}$ are independently selected from hydrogen, substituted or unsubstituted alkyl, substituted or unsubstituted alkenyl, substituted or unsubstituted alkynyl, substituted or unsubstituted aryl, substituted or unsubstituted aminoalkyl, substituted or unsubstituted aminoalkenyl, substituted or unsubstituted aminoalkynyl, and substituted or unsubstituted aminoaryl, provided that at least one of $R_{19}$ and $R_{20}$ includes an amino group.

* * * * *